United States Patent [19]

Maschmeyer et al.

[11] Patent Number: 4,484,016
[45] Date of Patent: Nov. 20, 1984

[54] PROCESS FOR MAKING A MIXTURE OF ETHYLENE AND BUTENE-1

[75] Inventors: Donald M. Maschmeyer; Allan E. Fowler, both of Lake Jackson; Steve A. Sims, Angleton; G. Eldon White, Lake Jackson, all of Tex.

[73] Assignee: The Dow Chemical Company, Midland, Mich.

[21] Appl. No.: 510,538

[22] Filed: Jul. 5, 1983

[51] Int. Cl.³ .............................................. C07C 2/04
[52] U.S. Cl. ..................................... 585/510; 585/328; 585/522; 585/637
[58] Field of Search ................ 585/328, 522, 637, 510

[56] References Cited

U.S. PATENT DOCUMENTS

| | | | |
|---|---|---|---|
| 3,721,719 | 3/1973 | Fernald et al. | 585/522 |
| 4,314,090 | 2/1982 | Shewbart et al. | 585/637 |
| 4,380,684 | 4/1983 | Fowler et al. | 585/637 |

Primary Examiner—Curtis R. Davis
Attorney, Agent, or Firm—B. G. Colley

[57] ABSTRACT

Butene-1 and ethylene mixtures are made by reacting ethylene with a trialkyl aluminum in a boiling bed reactor. The process is more efficient in that it is selective for making butene-1 and more butene-1 is produced per unit weight of the trialkyl aluminum.

10 Claims, 1 Drawing Figure

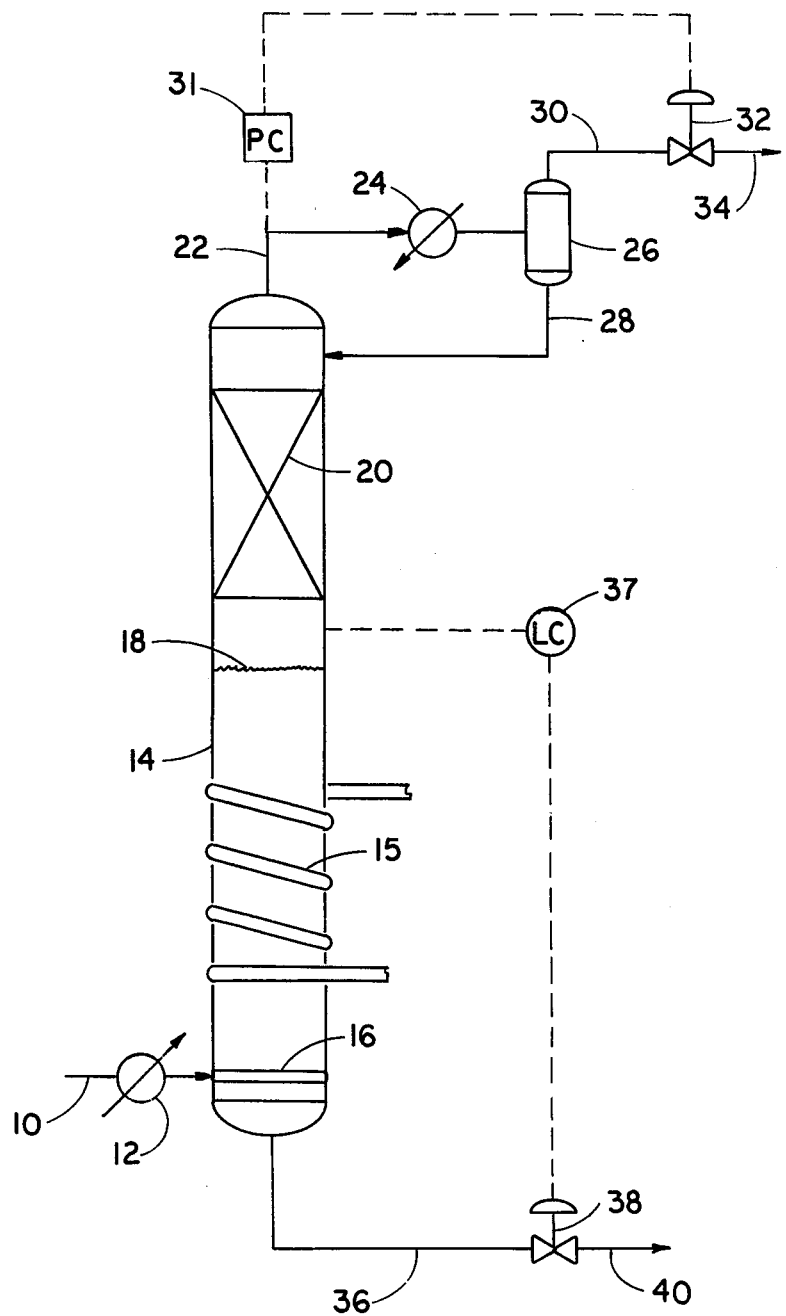

4,484,016

PROCESS FOR MAKING A MIXTURE OF ETHYLENE AND BUTENE-1

BACKGROUND OF THE INVENTION

This invention relates to a process for the preparation of a mixture of ethylene and butene-1.

It is known from U.S. Pat. No. 4,133,944, dated 1-9-79 (Col. 5 and 6) that ethylene copolymers can be prepared using a mixture of ethylene and butene-1 wherein the mixture is prepared in the polymerization reactor or in a separate dimerization stage before the polymerization reactor.

The selective dimerization of ethylene to butene-1 is known from U.S. Pat. No. 4,245,131 dated 1-13-81. The production of a mixture of ethylene, and higher alpha olefins using a coil reactor is disclosed in U.S. Pat. No. 3,721,719, dated 3-20-73. However, the instant process is selective for the production of butene-1 and gives a higher butene-1 to trialkyl aluminum ratio, i.e., more weight of product per unit weight of catalyst.

SUMMARY OF THE INVENTION

This invention relates to a process for making a mixture comprising ethylene and butene-1 wherein ethylene is reacted with an excess of a dilute trialkyl aluminum solution in a solvent therefore under a pressure in the range from 100 to 1500 psig and preferably 300 to 600 psig, a temperature in the range from 200° to 325° C. and preferably 250° to 280° C., an ethylene to trialkyl aluminum weight ratio in the range from 200:1 to 20,000:1 and preferably 4000:1 to 8000:1. The reaction is conducted in a vertical reaction zone with the contact between the ethylene and the trialkyl aluminum solution taking place at the lower end of the reaction zone. This reaction raises the temperature of the reactants to the boiling point of the solvent whereby the reactants vaporize and are condensed in the cooler upper end of the reaction zone. The solvents used are inert solvents such as alkanes or alkenes having 8 to 40 carbon atoms.

This reaction zone is called a boiling bed reaction zone for the purposes of this invention.

DESCRIPTION OF THE DRAWING

The drawing is a schematic description illustrating how the invention is carried out.

In the drawing, the ethylene gas inlet 10 flows into a preheater 12 and then into the vertical reactor 14. A gaseous diffuser or sparger 16 is provided to disperse or break up the ethylene gas for better contact. The level of the dilute solution of trialkyl aluminum in a hydrocarbon solvent is shown at 18. This level is maintained by the liquid controller 37 and its associated control valve 38.

If it is needed or desired a conventional heating device 15 is provided which can be an electric heating tape, fluid heating coils, or a reboiler.

In the upper end of the vertical reactor 14 there is provided a conventional contact device such as mesh packing, ceramic rings and other known contact devices.

The mixture of ethylene and butene-1 leaves the reactor 14 by line 22 where it is cooled by heat exchanger 24.

A reflux drum 26 provides for the condensation of solvent vapor and the liquid is returned to the reactor 14 by line 28.

The pressure in the reactor 14 is maintained within predetermined limits by the pressure controller 31 which regulates control valve 32.

The mixture of ethylene and butene-1 flows from the drum 26 through the control valve 32 into the outlet line 34.

DETAILED DESCRIPTION OF THE INVENTION

The following detailed examples are given for the purpose of further illustrating the invention.

EXAMPLE 1 (DB 29359-5)

High purity (99.9%) ethylene at 400 psig was sparged at 1.5 liters per minute (0.32 cm/sec.) through a stainless steel frit at the bottom of a 1 inch O.D. stainless steel pipe 54 inches long. A prepared solution of 0.4 wt. % triethylaluminum (TEA) in n-tetradecane was added to the reactor such that the liquid height was maintained at 2.7 inches. The liquid was recycled through a feed reservoir at a rate of 4 cc per minute. The liquid/gas mixture was heated to 277° C. by means of a variac controlled heating tape and reflux was provided by 3 inches of mesh packing in the top of the reactor. Overhead gases were passed through a wet test meter and vented. Analysis of the vent gases and TEA/solvent recycle were performed by gas chromatography. TEA catalyst concentration was based on measuring the ethane liberated by careful hydrolysis of solvent aliquots. After 300 minutes run time, a total of 120.2 g. of ethylene had been converted (25.7 wt. %) yielding 100.5 g. of forward flow $C_4$–$C_8$ oligomers. The product distribution in Table I was obtained:

TABLE I

| Forward Flow Product | Wt. (g) | Wt. % | Reaction Selectivity % |
|---|---|---|---|
| Ethylene | 346.0 | 77.5 | |
| Butene-1 | 95.8 | 21.5 | 95.5% |
| Butene-2 | 1.5 | 0.35 | 1.5% |
| Hexene-1 | 1.9 | 0.4 | 1.9% |
| Hexene-2 & Hexene-3 | 0.23 | 0.05 | 0.2% |
| 2-Ethyl-1-Butene | 0.95 | 0.1 | 0.9% |
| Octene-1 | 0.08 | 0.01 | 0.08% |
| 2-Ethyl-1-Hexene | 0.07 | 0.01 | 0.07% |
| Total | 446.53 | 99.92 | 100.15 |

The unit ratio for the grams butene-1 produced per gram TEA added was 159. A total of 19.7 g. (16.4%) of the converted product was lost to solvent.

EXAMPLES 2-15

Following the procedure outlined in Example 1, the results outlined in Table II and III were obtained:

TABLE II

| Ex. No. | Temp. (°C.) | Press. (psig) | Gas Res.[1] (sec) | Gas Velocity (cm/sec) | Solvent | TEA Conc. Wt. % | $C_2H_4$ Conv. (g.) | Wt.[2] Prod. (g.) |
|---|---|---|---|---|---|---|---|---|
| 2 | 261 | 400 | 47 | 0.36 | $C_{14}$ | 0.11 | 72.3 | 236.1 |
| 3 | 266 | 400 | 49 | 0.34 | $C_{14}$ | 0.11 | 135.6 | 458.4 |
| 4 | 273 | 400 | 77 | 0.31 | $C_{14}$ | 0.28[3] | 194.5 | 375.9 |

TABLE II-continued

| Ex. No. | Temp. (°C.) | Press. (psig) | Gas Res.[1] (sec) | Gas Velocity (cm/sec) | Solvent | TEA Conc. Wt. % | $C_2H_4$ Conv. (g.) | Wt.[2] Prod. (g.) |
| --- | --- | --- | --- | --- | --- | --- | --- | --- |
| 5 | 266 | 400 | 148 | 0.25 | $C_{14}$ | 0.10 | 218.2 | 241.7 |
| 6 | 273 | 400 | 61 | 0.27 | $C_{14}$ | 0.25 | 172.4 | 335.7 |
| 7 | 268 | 405 | 38.6 | 0.54 | $C_{14}$ | 0.29[3] | 428.6 | 1307.4 |
| 8 | 255 | 400 | 37 | 1.4 | $C_{14}$ | 0.27 | 1187.2 | 3039.7 |
| 9 | 260 | 410 | 39 | 1.32 | $C_{14}$ | 0.10 | 170 | 2355.8 |
| 10 | 250 | 400 | 60.6 | 0.78 | $C_{10}$—1 | 0.13 | 821.3 | 4046.3 |
| 11 | 250 | 400 | 59 | 0.82 | $C_{10}$ | 0.12 | 265.6 | 1667.6 |
| 12 | 247 | 400 | 62.7 | 0.77 | $C_{10}$ | 0.2 | 614.3 | 4720.6 |
| 13 | 248 | 410 | 46 | 1.15 | $C_{10}$ | 0.23 | 492.9 | 2889.0 |
| Control | 257 | 330 | 229 | 0.18 | $C_{14}$ | 0.25 | 156.3 | 70.6 |

[1] = residence time.
[2] = weight of product: total wt. of effluent gases during entire run.
[3] = tri n-butyl aluminum replaced the TEA.
$C_{14}$ = n-tetradecane.
$C_{10}$—1 = decene-1.
$C_{10}$ = n-decane.

TABLE III

| Ex. No. | PRODUCT COMPOSITION (Wt. %) | | | | | | Bte-1/TEA Unit Ratio |
| --- | --- | --- | --- | --- | --- | --- | --- |
| | $C_2H_4$ | Bte-1 | Hex-1 | Oct-1 | $C_{10}^{+[1]}$ | $BAO^{[2]}$ | $IO^{[3]}$ | |
| 2 | 76.9 | 21.9 | 0.4 | 0.01 | 0 | 0.2 | 0.3 | 219 |
| 3 | 77.9 | 20.2 | 0.7 | 0.03 | 0 | 1.1 | 0.5 | 324 |
| 4 | 65.0 | 31.5 | 1.0 | 0.02 | 0 | 1.2 | 1.3 | 154 |
| 5 | 60.8 | 32.7 | 1.4 | 0.04 | 0 | 2.15 | 2.9 | 556 |
| 6 | 65.7 | 29.1 | 1.1 | 0.04 | 0 | 2.1 | 1.8 | 279 |
| 7 | 71.4 | 25.3 | 1.7 | 0.04 | 0 | 1.0 | 0.5 | 801 |
| 8 | 62.5 | 31.0 | 2.9 | 0.2 | 0 | 1.0 | 0.8 | 879 |
| 9 | 93.2 | 5.5 | 1.0 | 0.1 | 0.02 | 0.1 | 0.05 | 291 |
| 10 | 84.0 | 13.5 | 1.5 | 0.04 | 0.23[4] | 0.2 | 0.09 | 1099 |
| 11 | 84.5 | 13.2 | 1.3 | 0.06 | 0.2[4] | 0.1 | 0.1 | 1554 |
| 12 | 87.2 | 10.8 | 1.3 | 0.09 | 0.2[4] | 0.2 | 0.05 | 500 |
| 13 | 82.3 | 13.8 | 2.0 | 0.15 | 0.3[4] | 0.03 | 0.09 | 1050 |
| Control | 60.7 | 28.5 | 0.7 | 0.16 | 0 | 2.3 | 6.7 | 67 |

Foot Notes:
[1]$C_{10}^+$ = hydrocarbons (especially olefins) having ten or more carbons.
[2]BAO = branched alpha olefins, e.g., 2-ethyl-1-butene.
[3]IO = internal olefins, e.g., butene-2.
[4]This $C_{10}^+$ material is solvent n-decane which is not refluxed back down the reactor.
Bte-1 = butene-1.
Hex-1 = hexene-1.
Oct-1 = octene-1.

We claim:

1. A process for making a mixture comprising ethylene and predominantly butene-1 which comprises reacting ethylene with a trialkyl aluminum in a solvent for the trialkyl aluminum in a boiling bed reaction zone under a pressure in the range from 100 to 1,500 psig, a temperature in the range from 200° to 325° C. with an ethylene to trialkyl aluminum weight ratio in the range from 200 to 20,000.

2. A process for making a mixture comprising ethylene and predominantly butene-1 which comprises reacting ethylene with a dilute trialkyl aluminum solution in an inert hydrocarbon in a boiling bed reaction zone under a pressure in the range from 100 to 1,500 psig, a temperature in the range from 200° to 325° C., with an ethylene to trialkyl aluminum weight ratio in the range from 2,500 to 10,000.

3. The process as set forth in claim 2 wherein the pressure range is 300 to 600 psig, the temperature range is 250° to 280° C., and the weight ratio range is 4,000 to 8,000.

4. A process for making a mixture comprising ethylene and predominantly butene-1 which comprises reacting ethylene with triethyl aluminum in an inert hydrocarbon solvent in a boiling bed reaction zone under a pressure in the range from 300 to 600 psig, a temperature in the range from 250° to 280° C., whereby the ethylene and triethyl aluminum weight ratio is in the range from 4,000 to 8,000.

5. The process as set forth in claim 4 wherein the reaction takes place in an inert hydrocarbon solvent having 8 to 40 carbon atoms.

6. A process for making a mixture comprising ethylene and predominantly butene-1 which comprises reacting an excess of ethylene with a dilute trialkyl aluminum solution in a solvent in a vertical reaction zone under a pressure in the range from 100 to 1,500 psig, a temperature in the range from 200° to 325° C. with an ethylene to trialkyl aluminum weight ratio in the range from 200 to 20,000 whereby said solvent is heated to the boiling point at the lower end of said reaction zone by said reaction and cooled below said boiling point at the upper end of said reaction zone.

7. A process for making a mixture comprising ethylene and predominantly butene-1 which comprises reacting an excess of ethylene with a dilute trialkyl aluminum solution in an inert hydrocarbon in a vertical reaction zone under a pressure in the range from 100 to 1,500 psig, a temperature in the range from 200° to 325° C., with an ethylene to trialkyl aluminum weight ratio in the range from 2,500 to 10,000 whereby said hydrocarbon is heated to the boiling point at the lower end of said zone by said reaction and cooled below said boiling point at the upper end of said zone.

8. The process as set forth in claim 7 wherein the pressure range is 300 to 600 psig, the temperature range is 250° to 280° C., and the weight ratio range is 4,000 to 8,000.

9. A process for making a mixture comprising ethylene and predominantly butene-1 which comprises reacting an excess of ethylene with a dilute triethyl aluminum solution in an inert hydrocarbon solvent in a boiling bed reaction zone under a pressure in the range from 300 to 600 psig, a temperature in the range from 250° to 280° C., whereby the ethylene and triethyl aluminum weight ratio is in the range from 4,000 to 8,000 whereby said solvent is heated to the boiling point at the lower end of said reaction zone by said reaction and cooled below said boiling point at the upper end of said reaction zone.

10. The process as set forth in claim 9 wherein the reaction takes place in an inert hydrocarbon solvent having 8 to 40 carbon atoms.

* * * * *